(12) United States Patent
Kawanaka

(10) Patent No.: US 6,349,230 B1
(45) Date of Patent: Feb. 19, 2002

(54) BLOOD MEASURING INSTRUMENT

(75) Inventor: Shoji Kawanaka, Kyoto (JP)

(73) Assignee: Kyoto Daiichi Kagaku Co., Ltd., Kyoto (JP)

(*) Notice: Subject to any disclaimer, the term of this patent is extended or adjusted under 35 U.S.C. 154(b) by 0 days.

(21) Appl. No.: 09/555,693

(22) PCT Filed: Feb. 25, 1999

(86) PCT No.: PCT/JP99/00906

§ 371 Date: Jun. 2, 2000

§ 102(e) Date: Jun. 2, 2000

(87) PCT Pub. No.: WO99/44048

PCT Pub. Date: Sep. 2, 1999

(30) Foreign Application Priority Data

Feb. 26, 1998 (JP) .............................................. 10-45130

(51) Int. Cl.⁷ ................................................. A61B 5/05
(52) U.S. Cl. ...................... 600/347; 600/345; 600/365; 204/403
(58) Field of Search ................................ 600/347, 345, 600/365; 204/403

(56) References Cited

U.S. PATENT DOCUMENTS 5,282,950 A * 2/1994 Dietze et al. ............... 204/406
5,288,636 A * 2/1994 Pollman et al. ............. 435/288
5,565,085 A * 10/1996 Ikeda et al. ............... 205/777.5

FOREIGN PATENT DOCUMENTS

| JP | 63-187150 | 1/1987 |
| JP | 1-284748 | 5/1988 |
| JP | 4-157449 | 7/1991 |
| JP | 4-357452 | 7/1991 |
| JP | 8-94571 | 9/1994 |
| JP | 9-166571 | 12/1995 |

* cited by examiner

Primary Examiner—Robert L. Nasser
Assistant Examiner—Patricia Mallari
(74) Attorney, Agent, or Firm—Merchant & Gould P.C.

(57) ABSTRACT

A blood measuring instrument for measuring a specific component of blood. The instrument has a platelike chip (2) for sucking sampled blood, and a measuring instrument body (1) including a connector (3) into which the chip (2) is plugged. The chip (2) has an enzyme electrode for delivering a response current when the enzyme reacts with a specific component of the blood. The measuring instrument body (1) includes two sets of connection terminals (21, 22) capable of being in contact with lead terminals on the chip (2), and the connection terminals (21, 22) of each set are opposed to each other. Therefore, the chip (2) can be plugged into the connector (3) and one of the connection terminals of each set can be brought into contact with the lead terminal even if the chip is upside down.

4 Claims, 3 Drawing Sheets

BLOOD MEASURING INSTRUMENT

FIELD OF THE INVENTION

The present invention relates to an instrument for measuring the concentration of a specific component of blood, in particular, to a blood sugar determining instrument for measuring the concentration of glucose in blood.

BACKGROUND OF THE INVENTION

In recent years, various kinds of biosensors utilizing a specific catalytic action of enzymes have been developed to be used for clinical purposes. Most valuable use of such biosensors may be made in the area of e.g. diabetes treatment where it is vital for patients to keep their blood glucose concentration ("blood sugar level" below) within a normal range. For an inpatient, the blood sugar level can be kept normal under the supervision of the doctor. For an outpatient, self-control of the blood sugar level is an important factor for treatment in lack of doctor's direct supervision.

The self-control of the blood sugar level is achieved through a diet, exerciseand medication. These treatments may often be simultaneously employed under the supervision of the doctor. It has been found that the self-control works more effectively when the patient himself is able to check whether or not his blood sugar level is within the normal range.

Recently, blood sugar determining instruments have been used for self-checking of blood sugar level. As shown in FIG. 1, a blood sugar determining instrument mainly includes a main detecting unit 1 and a chip 2 for blood sugar measurement. As shown in FIGS. 2 and 3, the chip 2 includes a strip-like substrate 15 provided in its front portion with an electrode section 4. The electrode section 4 is covered by a reaction layer 5, a spacer 6 and a cover sheet 7. The electrode section 4 is provided with an operational terminal 11 and a counterpart terminal 12 surrounding the operational terminal 11. The operational terminal 11 and the counterpart terminal 12 are electrically connected to lead terminals 13 and 14, respectively, which are formed on a base end portion of the substrate 15. The reaction layer 5, which covers the electrode section 4, contains potassium ferricyanide and an oxidase such as glucose oxidase.

The blood measuring instrument may be used in the following manner. A patient pricks his or her own skin with e.g. a lancet for oozing blood. Then, the oozed-out blood is caused to touch the tip of the chip 2 plugged into the detecting unit 1. The blood is partially sucked into the reaction layer 5 by capillary action. The reaction layer 5, disposed above the electrode section 4, is dissolved by the blood, which starts an elementary reaction.

The potassium ferricyanide contained in the reaction layer 5 is reduced, whereas potassium ferrocyanide or reduced electron carrier is accumulated. The amount of the potassium ferrocyanide is proportional to the concentration of glucose to be measured. When the potassium ferrocyanide accumulated for a specific time is electrochemically oxidized by application of a certain voltage, a response current will pass through the operational terminal 11. Thus, the glucose concentration (blood sugar level) is determined by measuring the response current with the detecting unit 1. As shown in FIG. 6a, the chip 2 is plugged into a connector 3. The connector 3 is internally provided with connection terminals 21 to come into contact with the lead terminals 13, 14 for detection of the response current flowing through the operational terminal 11. The detected current is converted into a glucose concentration value by a computer incorporated in the detecting unit 1.

The terminals 11, 12, 13, 14 on the chip 2 are formed only on one side of the chip 2, so that these terminals 11, 12, 13, 14 are readily formed by screen printing. Thus, the manufacturing process is preferably simplified, which serves to lower the costs of consumable chips.

However, the one-side formation of the terminals 11, 12, 13, 14 can be disadvantageous in inserting the chip 2 into the connector 3 of the detecting unit 1 upside down. As shown in FIG. 6b, the lead terminals 13, 14 on the chip 2 may fail to be connected to the connection terminals 21 in the connector 3. In such an instance, proper measurement cannot be performed by the blood sugar determining instrument.

Diabetics may often be elderly people and/or have weak eyes, so that many of them may have difficulty in distinguishing one surface of the chip 2 from the other. In light of this, the chip 2 may be provided with side-discerning means. For instance, the chip 2 may be provided with a cut out or protrusion formed on one side. Alternatively, the measuring instrument may be so arranged that the chip 2, when held upside down, cannot be inserted into the detecting unit. In any case, the chip needs to be inserted properly, i.e., without having its obverse and reverse surfaces turned over. Disadvantageously, the formation of a cutout or protrusion will require additional steps for making the chips, which results in a cost increase.

It is an object of the present invention to provide a blood measuring instrument, wherein a chip can be inserted into a detecting unit without undergoing the surface-discerning step.

SUMMARY OF THE INVENTION

A blood measuring instrument according to the present invention comprises: a plate-like chip for drawing sampled blood; and a main detecting unit having a connector into which the chip is inserted. The chip includes, on a single side, an enzyme electrode section for passing a response current in response to a specific component of the blood, and lead terminals electrically connected to the enzyme electrode section. The main detecting unit includes two sets of connection terminals which are disposed within the connector and engageable with the lead terminals of the chip, wherein the two sets of connection terminals are held infacing relation to each other.

According to the present invention, the connector of the main detecting unit is internally provided with two sets of connection terminals engageable with the lead terminals on the chip, and these two sets of connection terminals are held in facing relation to each other. When the chip is plugged into the connector, either one of the two sets of connection terminals is connected to the lead terminals formed on a selected side of the chip. Thus, proper blood measurement is carried out whether the chip inserted into the main detecting unit faces upward or downward.

In a preferred embodiment, the enzyme electrode section includes a reaction layer dissolved by the blood and an electrode pattern which has an operational terminal for passing the response current and a counterpart terminal surrounding the operational terminal. The reaction layer covers the operational terminal of the electrode pattern.

When the blood is applied onto the chip, the reaction layer is dissolved by the blood, which starts an enzyme reaction. Thus, electron carriers are generated correspondingly to the concentration of the specific component (e.g. glucose) of the blood. After a certain period of time, a voltage is applied to the chip, whereby a response current is generated in the operational terminal of the electrode section. For measurement, the response current is supplied to the main detecting unit through the lead terminals and the connection terminals of the connector. The response current is proportional to the concentration of the specific component of the blood. Thus, the concentration of the specific component is calculated on the basis of the response current value by using a calibration curve prepared beforehand.

In a preferred embodiment, the reaction layer contains glucose oxidase or lactate oxidase as an oxidase and potassium ferricyanide as an electron acceptor.

For determining the glucose concentration in blood (blood sugar), the oxidase in the reaction layer is glucose oxidase and the electron carrier is potassium ferricyanide. In enzyme reaction, the glucose is turned to be gluconic acid, while the potassium ferricyanide is reduced to potassium ferrocyanide. The amount of potassium ferrocyanide is proportional to the concentration of the glucose to be measured. After a predetermined period of time, the potassium ferrocyanide is electrochemically oxidized by applying a voltage to the chip. Then, the resulting response current is converted to the glucose concentration.

For determining the lactic acid concentration, the oxidase in the reaction layer is lactate oxidase, while the electron carrier is potassium ferricyanide. In enzyme reaction, the lactic acid is turned to be pyruvic acid, while the potassium ferricyanide is reduced to potassium ferrocyanide. The amount of the potassium ferrocyanide is proportional to the concentration of the lactic acid to be measured. After a certain time, the potassium ferrocyanide is electrochemically oxidized by applying a voltage to the chip. Then, the amount of the resulting response current is converted to the lactic acid concentration.

As described above, according to the blood measuring instrument of the present invention, it is unnecessary to worry about whether or not the chip is held upside down in inserting the chip into the connector of the main detecting unit. It is much easier for weak-sighted or elderly patients to use the blood measuring instrument of the present invention than the conventional instrument, since there is no need to check the orientation of the obverse or reverse surface of the chip.

Other features and advantages of the present invention will become apparent from the detailed description given below with reference to the accompanying drawings.

BEST MODE FOR CARRYING OUT THE INVENTION

Figure 1:
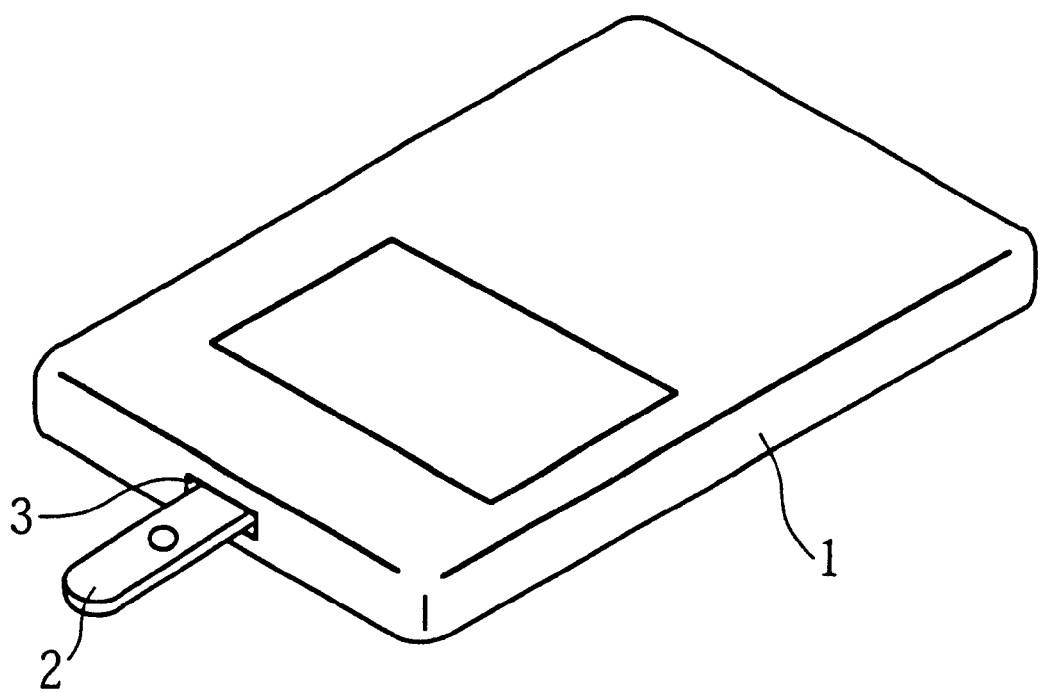
FIG. 1 is a perspective view showing the external appearance of a blood measuring instrument according to an embodiment of the present invention.

An embodiment of the present invention will be described with reference to the accompanying drawings. As shown in FIG. 1, a blood measuring instrument includes a main detecting unit 1 and a disposable plate-like chip 2 to be plugged into the main detecting unit 1 in use.

Figure 2:
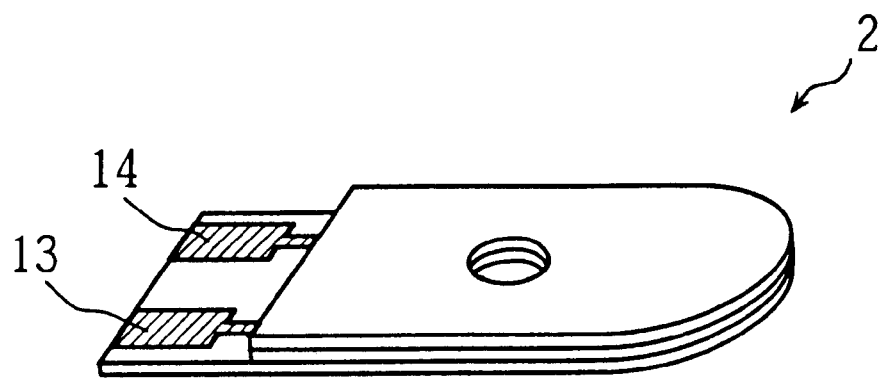
FIG. 2 is a perspective view showing the entirety of a chip used for the blood measuring instrument.
Figure 3:
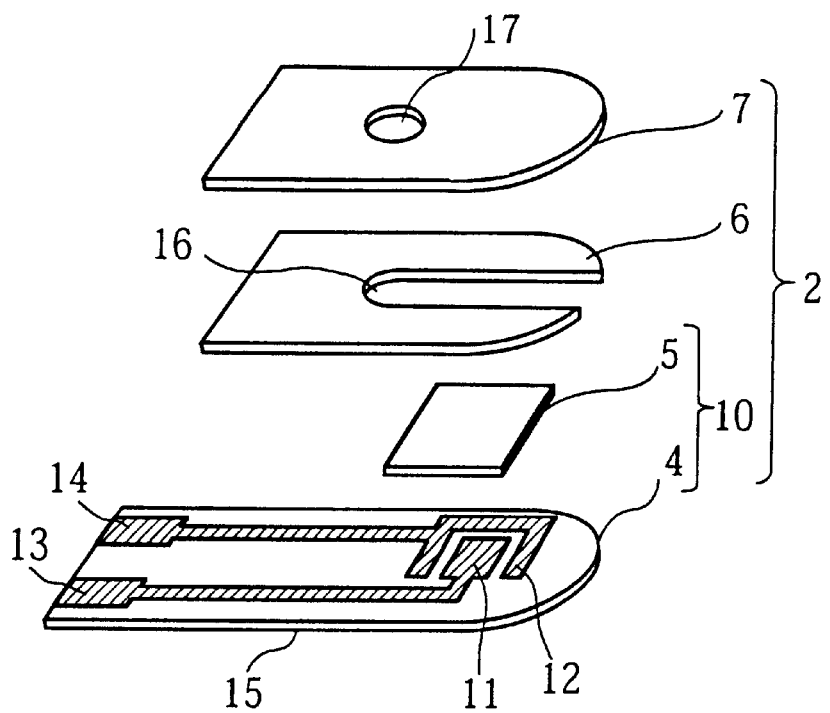
FIG. 3 is an exploded, perspective view showing the chip used for the blood measuring instrument.
Figure 4A:
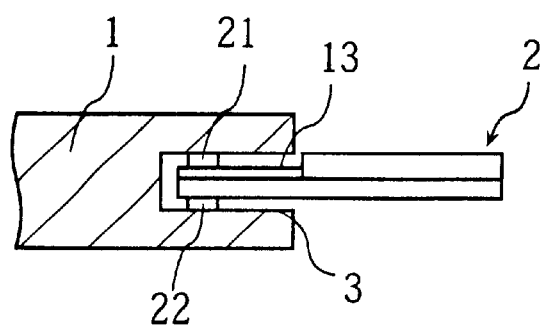
FIGS. 4a and 4b are enlarged, partial sectional views showing how the chip engages with a main detecting unit of the blood measuring instrument of the present invention.
Figure 4B:
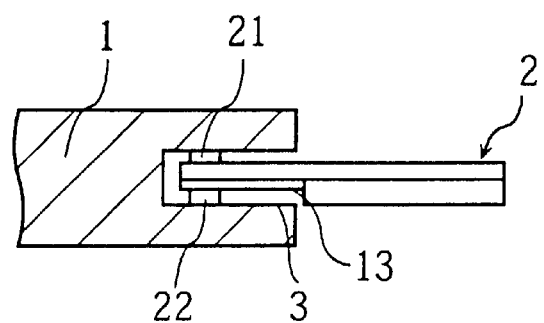

In carrying out the present invention, the conventional basic arrangements may be applicable to the chip 2 without any changes. As shown in FIGS. 2 and 3, the chip 2 has a strip-like shape as a whole, while also including a surface whose front end portion is provided with an enzyme electrode section 10 and whose base end portion is provided with two lead terminals 13, 14. Preferably, the lead terminals 13, 14 may be made of silver. The enzyme electrode section 10 includes an electrode pattern 4 and a reaction layer 5 arranged thereon. The electrode pattern has a carbon operational terminal 11 and a carbon counterpart terminal 12 surrounding the operational terminal. The operational terminal 11 is electrically connected to one lead terminal 13, while the counterpart terminal 12 is electrically connected to the other lead terminal 14. The terminals 11, 12, 13, 14 may be formed by screen printing on a substrate made of poly (ethylene terephthalate). A spacer 6 and a cover sheet 7 are attached to cover the reaction layer 5. The spacer is formed with a slit 16 open at the front end portion, while the cover sheet 7 is formed with an air hole 17. Thus, after being applied onto the tip of the chip 2, sample liquid such as blood is sucked into the passage of the slit 16 by capillary action and led to the reaction layer 5.

The reaction layer 5 is a plate-like element made of dried aqueous solution containing oxidase (glucose oxidase), potassium ferricyanide and carboxymethyl cellulose.

The main detecting unit 1 is provided with a connector 3 into which the base end portion of the chip 2 is inserted. According to the present invention, the connector 3 is internally provided with two sets of connection terminals 21, 22 arranged in facing relation. In the illustrated embodiment, each set of the connection terminals 21, 22 includes two terminals. Thus, the lead terminals 13, 14 formed on the base end portion of the chip 2 are brought into proper contact with these terminals whether the obverse surface of the chip 2 faces upward or downward in insertion.

In use, the chip 2 is plugged into the connector 3 of the main detecting unit 1. According to the present invention, as described above, it does not matter whether the chip 2 faces upward or downward in insertion. Then, a cut is made in the skin with e.g. a lancet to ooze out a small amount of blood therefrom. Then, the blood is touched by the tip of the chip 2. The blood is then led to the enzyme electrode section 10 of the chip 2 by capillary action, as described above.

The reaction layer 5 of the enzyme electrode section 10 is dissolved by the supplied blood. Then, according to the enzyme reaction represented by the following formula, potassium ferrocyanide is produced in an amount corresponding to the glucose concentration. After a certain period of time, a predetermined voltage is applied on the chip 2. In response, a current is generated, which is proportional to the concentration of the potassium ferrocyanide produced by the enzyme reaction or to the concentration of the glucose. Therefore, the blood sugar level can be known by measuring the response current.

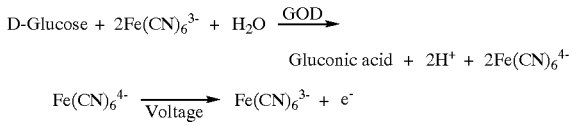

Figure 5:
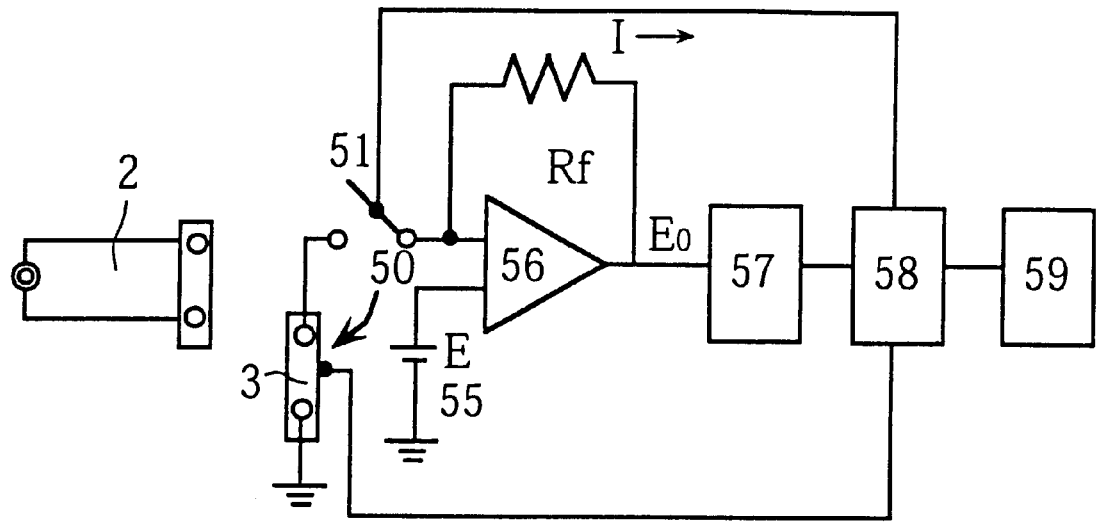
FIG. 5 is a block diagram showing an example of control circuit for the blood measuring instrument of the present invention.
Figure 6A:
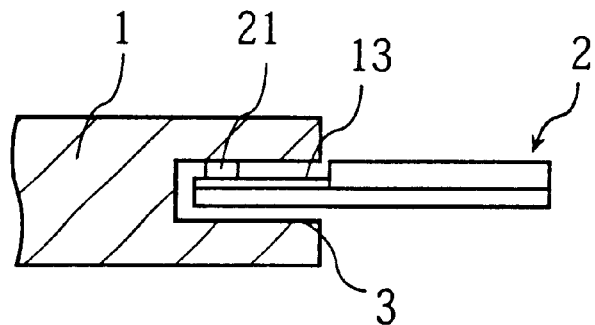
FIGS. 6a and 6b are enlarged, partial sectional views illustrating how the chip and the main detecting unit of a conventional blood measuring instrument.
Figure 6B:
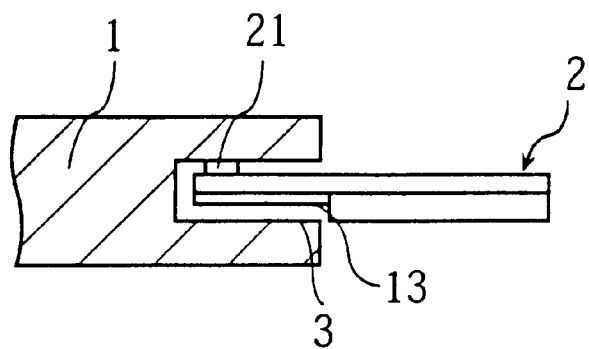

FIG. 5 shows an example of control circuit of the blood sugar determining instrument. When the chip 2 is plugged into the connector 3, a plugged-electrode sensing switch 50 detects the insertion of the chip, whereby a switch 51 is turned on automatically. Thus, a predetermined voltage is applied to the operational terminal 11 of the chip 2, which is electrically connected to the connection terminal 21 or connection terminal 22. The voltage to be applied is provided by a battery 55. The response current generated in the chip 2 set into the connector 3 is converted to voltage by a current/voltage converter 56 and then supplied to an A/D converter 57. A microcomputer 58 reads out an output signal from the A/D converter 57.

The enzyme electrode section of the chip 2 can be regarded as a resistor. When the resistance of the chip 2 is $R_s$, the amplification resistance of the current/voltage converter 56 is $R_f$, and the applied voltage is E, then the output voltage $E_0$ of the current/voltage converter 56 is given by the following equation:

$$E_0 = E + i \times R_f = E + (E/R_s) \times R_f$$

When no blood is supplied, the resistance $R_s$ of the chip 2 is extremely large or substantially infinite, while the current i is very small. Accordingly, the output voltage $E_0$ of the current/voltage converter 56 is nearly equal to E.

When blood is supplied to the chip 2, on the other hand, the resistance $R_s$ of the chip 2 decreases sharply, which causes a sharp increase in $E_0$. The absorption of the blood is detected by continuously monitoring the output voltage $E_0$ of the current/voltage converter 56.

Variations of the output voltage $E_0$ of the current/voltage converter 56 are analyzed by the microcomputer 58 via the A/D converter 57. Thus, upon sharp increase of $E_0$ (or sharp decrease of $R_s$), the timer of the measuring instrument is automatically started. At the same time, the switch 51 is turned off. The once-opened switch 51 is closed again later, namely, after the above-mentioned enzyme reaction has occurred. Thus, required voltage is applied to the operational terminal 11. Then, the response current generated at this stage is measured to be used for calculation of glucose concentration based on a prescribed calibration curve. The result is displayed on a display 59.

In the above embodiment, the blood measuring instrument of the present invention determines the concentration of glucose in blood (blood sugar). However, the same blood measuring instrument may be applicable to determinations of other components. When the oxidase contained in the reaction layer 5 is lactate oxidase, the blood measuring instrument can be utilized for determination of the lactic acid concentration. In this case, the chip may be supplied with saliva since an appropriate amount of lactic acid is secreted in saliva. Though saliva has a weaker buffer action than blood, it is possible to determine the lactic acid concentration of saliva when buffer agent is added to the reaction layer 5 of the chip 2.

As shown in FIGS. 2 and 3, the electrode pattern 4 of the chip 2 is formed on the front end portion of the strip-like substrate 15, and the electrode pattern 4 is covered by the reaction layer 5, spacer 6, and cover sheet 7. The electrode pattern 4 includes the operational terminal 11 and the counterpart terminal 12 surrounding the operational terminal 11. The operational terminal 11 and the counterpart terminal 12 are electrically connected to the lead terminal 13 and the lead terminal 14, respectively, which are formed on the base end portion of the substrate 15. The reaction layer 5 covering the electrode pattern 4 contains potassium ferricyanide and an oxidase or glucose oxidase.

Without being limited to the above, the present invention may be varied in many ways within the scope of the appended claims, and the variation may include equivalent replacement each element.

What is claimed is:

1. A blood measuring instrument comprising: a plate-like chip for drawing sampled blood; and a main detecting unit having a connector into which the chip is inserted;

wherein the chip includes, on a single side, an enzyme electrode section for passing a response current in response to a specific component of the blood, and lead terminals electrically connected to the enzyme electrode section; and wherein the main detecting unit includes two sets of connection terminals which are disposed within the connector and engageable with the lead terminals of the chip, the two sets of connection terminals being spaced from each other in a thickness direction of the chip and held in facing relation to each other.

2. The blood measuring instrument according to claim 1, wherein the enzyme electrode section comprises a reaction layer dissolved by the blood and an electrode pattern which includes an operational terminal for passing the response current and a counterpart terminal surrounding the operational terminal, the reaction layer covering the operational terminal of the electrode pattern.

3. The blood measuring instrument according to claim 1, wherein the reaction layer contains glucose oxidase as an oxidase and potassium ferricyanide as an electron acceptor.

4. The blood measuring instrument according to claim 1, wherein the reaction layer contains lactate oxidase as an oxidase and potassium ferricyanide as an electron acceptors.

* * * * *